United States Patent [19]
Crockford et al.

[11] 4,424,200
[45] Jan. 3, 1984

[54] METHOD FOR RADIOLABELING PROTEINS WITH TECHNETIUM-99M

[75] Inventors: David R. Crockford, Haverhill, Mass.; Buck A. Rhodes, Albuquerque, N. Mex.

[73] Assignees: Nuc Med Inc., Albuquerque, N. Mex.; University Patents Inc., Norwalk, Conn.

[21] Appl. No.: 246,197

[22] Filed: Mar. 23, 1981

Related U.S. Application Data

[63] Continuation-in-part of Ser. No. 37,992, May 14, 1979, Pat. No. 4,323,546, which is a continuation-in-part of Ser. No. 908,568, May 22, 1978, abandoned.

[51] Int. Cl.$^3$ .................... A61K 43/00; A61K 49/00
[52] U.S. Cl. .............................................. 424/1.1; 424/9
[58] Field of Search ........................... 424/1, 115, 9

[56] References Cited

U.S. PATENT DOCUMENTS

| | | |
|---|---|---|
| 3,872,226 | 3/1975 | Haney et al. ............................ 424/1 |
| 4,042,677 | 8/1977 | Molinski et al. ........................ 424/1 |
| 4,070,493 | 1/1978 | Nadeau .................................... 424/1 |
| 4,247,534 | 1/1981 | Bevan ..................................... 424/1.5 |

OTHER PUBLICATIONS

McManus et al, Can. Res., 36, pp. 2367–3481, Sep. 1976.

Wong et al, Int. J. Appl. Rad. Isotopes, 29, 251–253, 1978.

*Primary Examiner*—Christine M. Nucker
*Attorney, Agent, or Firm*—Paul J. Cook

[57] ABSTRACT

Proteins are radiolabeled with technetium-99m in a reducing environment comprising buffered stannous chloride wherein the tin utilized to form the stannous chloride is non-oxidized, the buffered stannous chloride is purged of oxygen and the buffer comprises an alkali metal biphthalate and an alkali metal tartrate.

Proteins which have been preincubated with tin are radiolabeled with technetium-99m to form a strongly bonded, non-exchangeable radiolabeled tracer substance. The radiolabeling can be accomplished immediately after pretinning, or the pretinned proteins can be freeze-dried and the radiolabeling accomplished at some time in the future when the pretinned proteins are resolubilized in a saline solution of sodium pertechnetate - TC-99m. Pretinning can be accomplished in a reducing environment comprising stannous chloride buffered with an alkali metal biphthalate and an alkali metal tartrate, this solution having been purged of oxygen to assure that the stannous chloride is non-oxidized. When the pretinning proteins are freeze-dried, they can be utilized to prepare instant TC-99m labeling kits for use as radiopharmaceuticals.

17 Claims, 3 Drawing Figures

METHOD FOR RADIOLABELING PROTEINS WITH TECHNETIUM-99M

REFERENCE TO RELATED APPLICATIONS

This application is a continuation-in-part of Ser. No. 037,992, filed May 14, 1979, now U.S. Pat. No. 4,323,546 which in turn is a continuation-in-part of Ser. No. 908,568, filed May 22, 1978, abandoned.

BACKGROUND OF THE INVENTION

This invention relates to a method for radiolabeling proteins and chelating agents with technetium-99m into compositions produced therewith.

The use of compositions which emit radiation at levels which can be externally detected after administration to the human body are well known. These compositions are utilized to visualize and/or monitor functioning of various parts of the body or are utilized diagnostically to determine the presence and location of particular antigens, antibodies, hormones or the like. For example, such compositions have been utilized as bone scanning agents to determine the condition of the skeletal material. In another example, radiolabeled antibodies are utilized to detect tumors having associated therewith carcinoembryonic antigen. As disclosed in U.S. Pat. Nos. 3,663,684, 3,867,363 and 3,927,193, $I^{131}$ or $I^{125}$ labeled antibodies to carcinoembryonic antigen are utilized to detect tumors which produced or are associated with carcinoembryonic antigen. It is also well known that protein molecules can be tagged with technetimum-99m in order to form diagnostic agents.

Technetium-99m has been utilized to radiolabel protein, chelating agents, phosphonate bone scanning compositions or the like by a technique which utilizes sodium pertechnetate wherein the technetium initially is in the +7 state. In these procedures, the pertechnetate is contacted with a reducing agent, preferably stannous chloride in order to reduce the technetium to the +3, +4 or +5 oxidation state in the presence of the protein, chelating agent or the like which is to be radiolabeled. It is necessary to maintain the technetium in the reduced state in order to maintain the chemical bond between the technetium molecule and the substrate being radiolabeled. However, it is also necessary that the reduced technetium not become hydrolyzed after reduction, as this forms an insoluble technetium oxide or hydroxide which, when administered to the patient, is automatically deposited in the liver, bone marrow and/or spleen rather than in those regions of the body where concentration of the technetium is desired. It is also necessary that the technetium is firmly bound to the protein such that the reduced technetium is not transferred to buffer molecules or to other proteins as small molecules in the patient's blood. Otherwise, upon administration, the technetium will not migrate to the desired part of the body. Finally, it is essential that the technetium bond be of sufficient strength so that technetiumlabel is not transferred to other molecules before it can be localized in the desired part of the body.

Prior to the present invention, great difficulty has been experienced in maintaining the stability of substrates labeled with technetium-99m. This is due primarily to problems associated with oxidation during formation of the labeled substrate and/or the use of buffering compositions which cause the reducing stannous ion to precipitate from the labeling solution. Prior to the present invention, compositions containing a substrate to be radiolabeled with technetium-99m have been generally unstable so that they do not retain radiochemical purity either during storage or after being adminstered to the patient. Accordingly, it would be highly desirable to provide substrate compositions having high stability and which are capable of being radiolabeled with technetium-99m in a manner so that both the complex state and the oxidation state of the technetium-99m can be properly maintained and stability assured. Previously, some methods of labeling of the proteins have altered the biological properties of the proteins by denaturation or reduction of their ability to participate in immunochemical reactions, or in the case of immunoglobulin or antibodies, reduced reactivity with their respective antigens.

SUMMARY OF THE INVENTION

In accordance with this invention, a substrate to be radiolabeled with technetium-99m is admixed with a buffered stannous chloride composition having a pH between about 4.5 and about 8.5 wherein the stannous chloride is produced from a non-oxidized tin source, the buffered stannous chloride is purged of oxygen and the buffer comprises a mixture of alkali metal biphthalate and an alkali metal tartrate. Alternatively, the buffer may include alkali metal borate or gentisate. The stannous chloride is prepared by reacting concentrated hydrochloric acid with tin substantially free of oxygen to form a stannous chloride solution substantially free of oxygen. This is accomplished conveniently by purging all solutions and the working environment with an inert gas or nitrogen. The stannous chloride solution then is admixed with the buffer and the resultant mixture then is neutralized with sodium hydroxide. The neutralized solution then is admixed with the substrate eventually to be radiolabeled with technetium-99m. This solution is allowed to incubate for several hours (usually over 15 hours) in the absence of oxygen and at room temperature. Alternately higher or lower incubation temperatures may be used with a corresponding change in the incubation time, i.e., if the incubation temperature is 35° C., then the incubation time may be reduced by approximately one-half, or if the incubation temperature is 15° C., then the incubation time must be doubled. In any event, the incubation temperature used should not cause degradation of the compound being pretreated with the tin. This solution then is admixed with sodium pertechnetate-Tc99m while avoiding the introduction of atmospheric oxygen to yield radiolabeled substance. Prior to contact with the sodium pertechnetate, the substrate-stannous chloride-buffer solution can be lyophilized and subsequently reconstituted when radiolabeling is desired. A kit also is provided which includes the buffer, stannous chloride and substrate. The kit also may contain a chromatographic column containing a material capable of binding technetium as the pertechnetate, reduced hydrolyzed technetium, colloidal technetium or weakly complexed technetium as well as being capable of binding a reducing agent which reduces technetium +7 to technetium +4−+5.

DESCRIPTION OF SPECIFIC EMBODIMENTS

Figure 1:
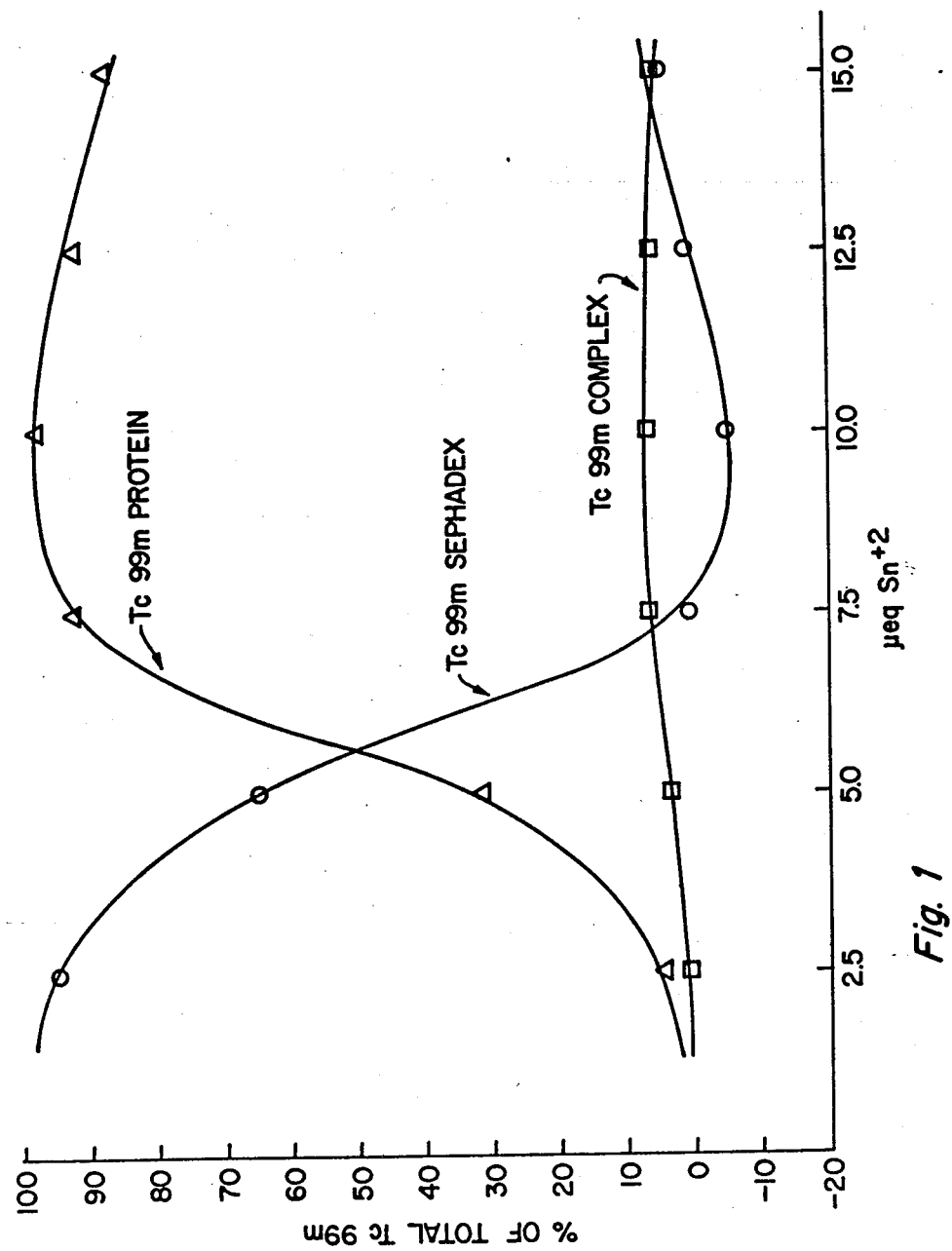
FIG. 1 shows the relationship between tin concentration and final technetium-labeled protein produced.

The stannous chloride reducing agent is prepared either from non-oxidized solid tin pellets by contact thereof with concentrated hydrochloric acid or can be prepared from any other source of tin such as stannous chloride or fluoride. In the latter instance, the resultant stannous chloride solution is purged of oxygen prior to addition thereof to the substrate. This can be accomplished conveniently by bubbling an inert gas through the stannous chloride solution such as nitrogen, helium or the like. This initial purging step may not be required when utilizing a non-oxidized solid tin source.

The buffer comprises a solution of alkali metal biphthalate and an alkali metal tartrate which may include sodium borate or sodium gentisate. The preferred biphthalates are potassium biphthalate, sodium biphthalate or mixtures thereof and the preferred tartrates are sodium tartrate, potassium tartrate or mixtures thereof. The molar ratio of biphthalate to tartrate is between about 1 and about 10, preferably between about 2 and about 3. It has been found that when utilizing this particular buffering composition, little or no reaction thereof with stannous chloride occurs. Thus, the stannous chloride is free to act as a reducing agent for the technetium. After the buffering composition and the stannous chloride composition have been admixed, the resultant composition is neutralized to a pH of between about 4.5 and about 8.5 by adding sodium hydroxide thereto.

The substrate which is to be subsequently radiolabeled with technetium-99m then is added to the buffered reducing agent and then is allowed to stand at about room temperature in the absence of atmospheric oxygen for at least about 15 hours, preferably about 21 hours. If desired, this solution can be heated moderately to reduce the incubation time. The solution then can be either freeze-dried and subsequently reconstituted for admixture with pertechnetate or can be admixed directly with pertechnetate solution to obtain the labeled substrate. If desired, the resultant radiolabeled substrate may be further purified to separate the labeled substrate from free technetium such as by chromatography in a Sephadex column or a Sepharose column pretreated with a saturated solution of stannous biphthalate. However, this last step is not necessary. In any event, this step is conducted while avoiding or minimizing the introduction of atmospheric oxygen. Typical results obtained with the present invention are shown in Table I.

TABLE I

| Protein | % Yield of Sephadex Column Chromatographically Purified Tc-99m Labeled Protein | Percent Reduced Tc-99m |
|---|---|---|
| Human Serum Albumin - 200 mCi of Tc-99m | 62 | 99.3 |
| Bovine Gamma Globulin - 2.0 mCi of Tc-99m | 78 | 99.9 |
| Bovine Gamma Globulin - 200 mCi of Tc-99m | 88 | 99.7 |

The source of the technetium-99m preferably is water soluble such as the alkali metal pertechnetate. The technetium can be obtained as sodium pertechnetate Tc-99m from a conventional 99Mo/99mTc generator. Any source of pharmaceutically acceptable technetium-99m may be utilized in the present invention.

Any protein, chelating agent or other substrate that normally is labeled with technetium-99m can be radiolabeled in accordance with this invention. Representative suitable substrates include IgG, the Fab fragments of IgG, human chorionic gonadotropin (hCG), anti-hCG or anti-hCG-beta, antibodies to anti-hCG or antibodies to anti-hCG-beta, fibrinogen, urokinase, alpha-fetoprotein, carcinoembryonic antigen (CEA), anti-CEA, human serum albumin (HSA) or other proteins.

The present invention also provides a kit with which a user can prepare the compositions of this invention and administer it to a patient relatively quickly after preparation. The kit includes the substrate either in a lyophilized form, frozen, or liquid of suitable ionic strength and pH, and either containing or not containing the stannous chloride or fluoride reducing agent. If not premixed with the stannous chloride or fluoride, the substrate can be admixed with the stannous chloride or stannous fluoride separately provided within the kit and in a separate container. The stannous chloride can be admixed with the buffer or the buffer can be stored in a separate container in lyophilized form or the like. It is preferred that the substrate, stannous chloride and buffer as well as the neutralizing agent be stored in a common container in lyophilized form for convenience of use. Thus, when this composition is reconstituted with sodium pertechnetate-Tc99m, it has a reducing pH of about 3 to about 5.5 when combined with technetium-99m as the pertechnetate. The solution of labeled substrate then is suitable for administration to a patient. The present invention also provides a new composition of matter comprising the product of the protein incubated with stannous ion wherein the concentration of stannous ion is sufficiently high to assure subsequent strong bonding of at least about 70% of bondable technetium-99m. As shown in FIG. 1, to attain this degree of technetium binding, at least about 6.0 milliequivalents of stannous ion is required. Also, as shown in FIG. 1, the preferred range of stannous ion concentration is between about 7.5 milliequivalents and about 12.5 milliequivalents. Additional stannous ion results in some formation of colloids which, while somewhat undesirable, can be easily removed by filtration.

In an alternative embodiment of this invention, the kit can include a container for a column of material which entraps or otherwise binds technetium-99m such as Sephadex, Sepharose or cellulose. The column of this material also can contain the reducing agent for technetium or the reducing agent can be added thereto when it is desired to reduce the technetium.

The labeled substrate is administered by intravenous injection in a pharmaceutically acceptable saline solution, sterile and pyrogen-free. Suitable dosages are usually between about 5 and 30 millicuries, preferably between about 10 and 20 millicuries of technetium-99m substrate for the normal 70 kg patient. The patient then can be scanned by conventional scintigraphy within about 1 hour to about 24 hours after administration of the labeled protein.

The following examples illustrate the present invention and are not intended to limit the same.

EXAMPLE I

This example illustrates the process of this invention for labeling immunoglobulin G (IgG). IgG is obtained from immunized animals such as sheep, goats, mice or humans. Sodium pertechnetate-Tc99m is obtained from New England Nuclear Corporation.

To 20 ml of a 40 mM potassium biphthalate/10 mM potassium and/or sodium tartrate solution (pH 5.6) was added 0.2 ml of 0.5 M stannous chloride in concentrated HCl (12 M). The stannous chloride was prepared by adding the concentrated hydrochloric acid to non-oxidized pellets of $SnCl_2$ having a surface free of dull stannous oxide. The pH of the resultant solution then was brought up to 5.6 by adding 10 M NaOH thereto. 3.2 ml of this solution then was placed in a test tube to which was added 0.48 ml of the IgG (10 mg/ml in 0.9% NaCl). The test tube then was sealed to prevent introduction of atmospheric $O_2$ and was allowed to stand at room temperature for about 21 hours. After this incubation period, 2 ml of 99mTc as sodium pertechnetate was added to a 0.32 ml aliquot of the original mixture and the resultant mixture was allowed to stand an additional 30 minutes in order to permit the labeling reaction to come to equilibrium.

The results obtained are that 50 mCi or technetium-99m have been bonded to 150 micrograms or less of protein with greater than 90% of the radioactivity being with the IgG.

The method of this invention provides the following advantages:
a. Rapid labeling.
b. High specific activity in small volumes.
c. A preparation suitable for administration to humans.
d. Lower contamination with technetium which is not bonded to material being labeled.
e. Sufficient bond strength so that the technetium is not transferred to other molecules.

EXAMPLE II

This example illustrates a direct method of labeling to form the labeled anti-hCG-beta or anti-hCG. Anti-hCG or anti-hCG-beta is obtained from Serono Laboratories, Inc. Sodium pertechnetate-Tc99m is obtained from New England Corporation.

To 0.4 ml of a 50 mM of sodium-potassium tartrate buffer (pH 5.5) (10.51 g/l), pH adjusted to 5.50 with 50 mM tartaric acid is added 1.6 ml of a 50 mM potassium biphthalate buffer (pH 5.50) (10.21 g/l), pH adjusted to 5.50 with 10 N NaOH. To the resultant buffer solution is added 0.02 ml of 0.5 M $SnCl_2$-HCl (94.8 g/l conc. HCl). The resultant solution is titrated back to a pH of 5.65±0.05 by adding thereto 0.02 ml of 10 N NaOH and the resultant solution is adjusted to a pH of 5.65±0.05 with 1 N NaOH. To the solution is added 0.3 ml of a saline solution of anti-hCG or anti-hCG-beta (10 mg protein/ml saline). The reaction vessel is allowed to stand approximately 24 hours at room temperature. Thereafter, 0.2 ml of $NaTcO_4$ with an activity of about 20 millicuries is added to protein-containing composition and allowed to stand about 1 hour to effect substantially complete labeling of the protein prior to use. The resultant product is passed through a Sephadex column to remove free technetium from the labeled protein product.

EXAMPLE III

Following the procedure of Example I, the Fab fragment of IgG was substituted for the whole antibody. Yields from the Sephadex G-25-80 column chromatography showed about 80% recovery of Fab bound to technetium-99m. The labeled Fab antibody fragment can be converted into an instant technetiumlabeling kit. Single dosage kits were made which contain 150 micorgrams of the Fab (0.115 ml of the labeling mixture before lyophilization).

Analysis of the Fab kits was done with high speed chromatography with Sephacryl S-200 on a 2.5×95 cm column. The eluant was 10 mM sodium gentisate at pH 7. The chromatography was run in a 4° C. environment which, along with the anti-oxident effect of the gentisate, protected the technetium label against degradation. For each elution, 3 Fab kits were reconstituted, each with 0.5 ml of the equivalent of 50 mCi in decay technetium (Tc-99) with 50 microcuries of Tc-99m as the tracer. The kits were allowed to stand 1 hour after which the contents were combined and tested before chromatography according to the following procedure:

1. Fab kits' contents alone after reconstitution.
2. Fab kits with 3 ml 1% HSA added immediately after chromatography.
3. Fab kits' contents passed through a stannous-Sephadex filter immediately after chromatography.
4. Fab kits' contents passed through the stannous-Sephadex filter after reconstitution and addition of 1% HSA.

The chromatographic procedure was able to resolve distinctly the colloidal HSA Material, the non-colloidal HSA and the Fab fragments. The following table lists the yields for the 3 procedures.

TABLE II

| Filter | HSA | Fab | Colloid HSA | HSA | $TcO_4^-$ | Other |
|---|---|---|---|---|---|---|
| No | No | 33.5 | — | — | 2.8 | 63.7 |
| Yes | No | 15.8 | — | — | 1.4 | 82.8 |
| No | Yes | 30.0 | 4.5 | 2.6 | 3.3 | 59.6 |
| Yes | Yes | 25.1 | 5.5 | 2.2 | 2.4 | 64.8 |

As shown in Table II, this method can be used to prepare Tc99m labeled fragments (such as Fab) of IgG with only relatively small contaminations of colloidal or soluble HSA (human serum albumin). Without carrier HSA, there are significant losses of the labeled fragments on the filter. The low yields of Tc99m-Fab (15.8–33.5%) are an artifact of the Sephacryl column chromatography which is required to separate the Fab from the HSA fractions. Sephacryl reacts with Tc-Fab causing a loss of about ⅔'s of the product on the column.

EXAMPLE IV

Following the procedure in Example I (pretinning method), the method of Abramovici and Ermans, U.S. Pat. No. 4,057,617, 1977 (Basic Reduction Method) and the method of Molinski and Wilcaeniski, U.S. Pat. No. 4,042,626, 1977 (Stannous Tartrate Method), bovine gamma globulins were prepared and analyzed by Sephadex G150 column chromatography using 50 mM phthalate buffer saturated with stannous phthalate as the eluting solvent. The results are shown in Table III.

TABLE III

| Method | Total Yield of Radiolabeled IgG | % Reduced Tc | % Radiochemical Impurities Colloid Tc | Exchangeable Tc |
|---|---|---|---|---|
| Pretinning | 73 | 98 | 17 | 28 |
| Basic Reduction | 60 | 83 | 22 | 61 |
| Stannous Tartrate | 59 | 99 | 26 | 60 |

As shown in Table III, the method of this invention provides the following advantages:
1. Higher overall radiochemical yields.
2. Essentially complete reduction of the Tc (98%).
3. Lower radiochemical impurites, such as colloidal Tc-99m.
4. Lower percentage of exchangeable Tc-99m.

As shown in FIG. 1, in the pretinning method, the total amount of stannous ions can be varied to provide the optimum microequivalents of $Sn^{+2}$ to give the optimum yield of radiolabeled protein.

Figure 2:
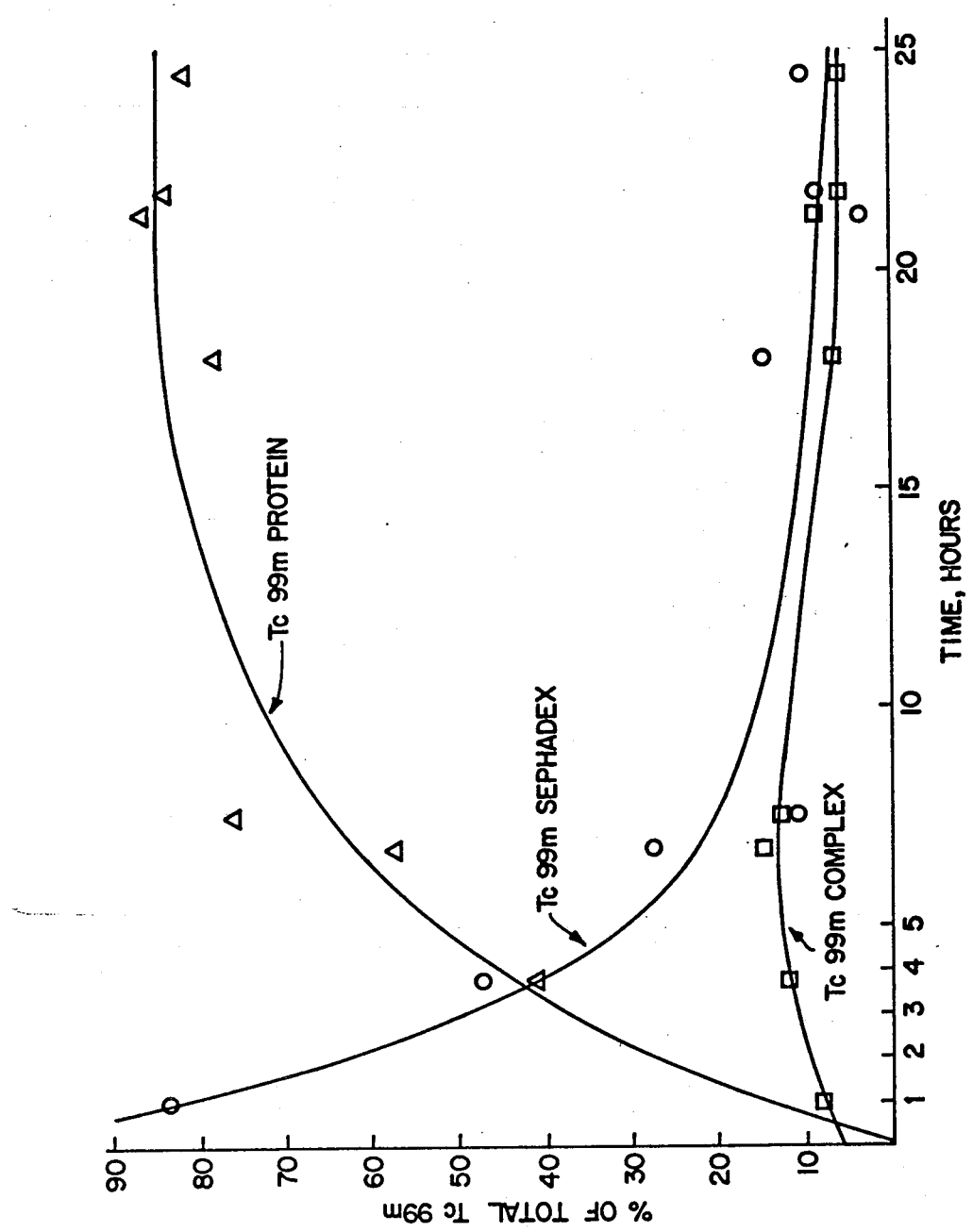
FIG. 2 shows the relationship between pretinning incubation time and percent technetium bound to protein.

As shown in FIG. 2, in the pretinning method, the incubation time, i.e., the duration of pretinning at 25° C. is about 21 hours or greater.

Figure 3:
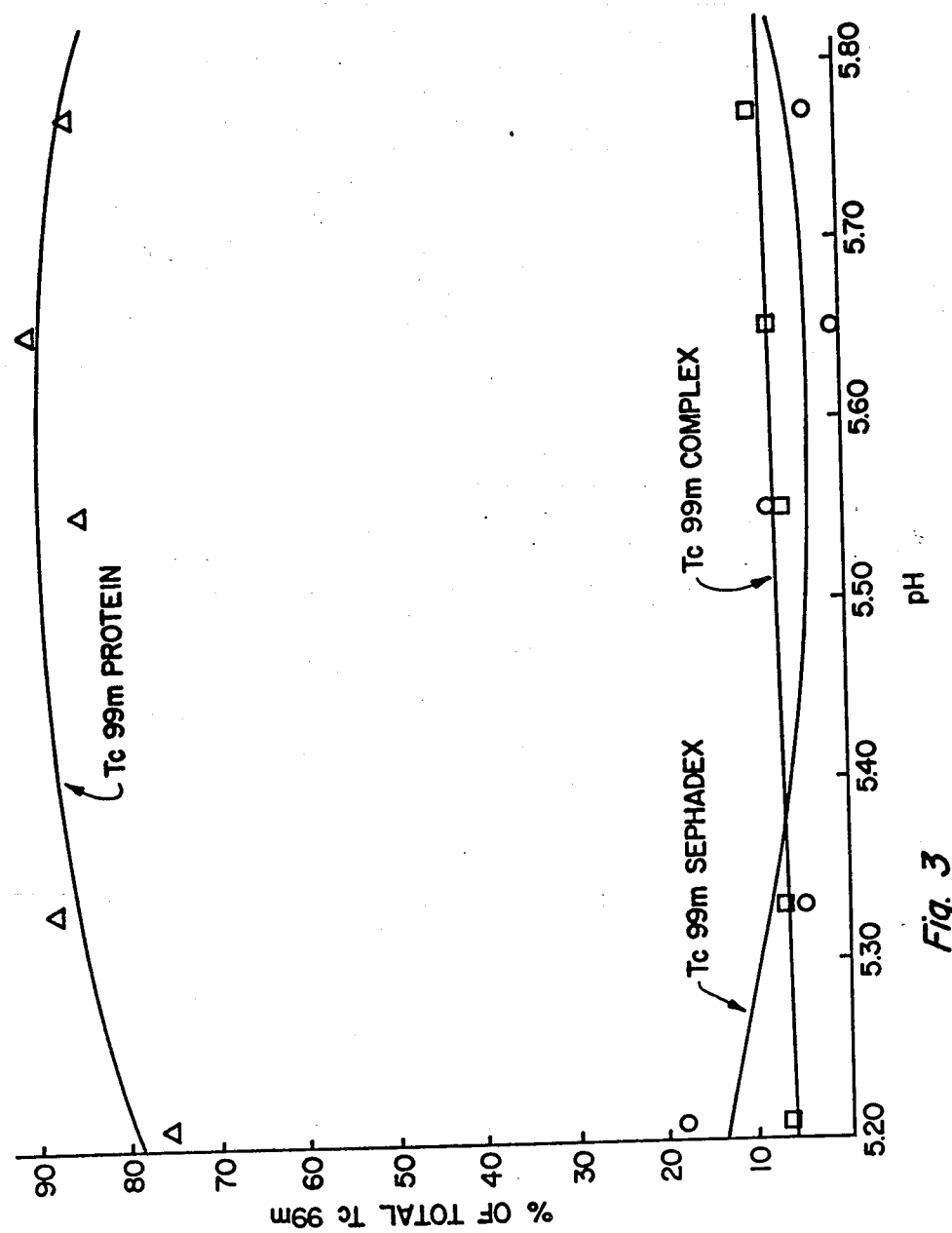
FIG. 3 shows the relationship between pH and percent technetium bound to protein.

As shown in FIG. 3, in the pretinning method, the pH is varied to show that the optimum pH for the labeling of bovine gamma globulin is between 5.5 and 5.6.

We claim:

1. The process for forming a reducing composition suitable for being radiolabeled with technetium-99m which comprises incubating a source of stannous ion with a protein in the presence of a buffering composition comprising a mixture of an alkali metal biphthalate and an alkali metal tartrate having a pH between about 4.5 and 8.5 for at least about 15 hours at a temperature wherein said protein is not denatured.

2. The process of claim 1 wherein said mixture is incubated for at least about 21 hours.

3. The process of any one of claims 1 or 2 wherein said buffering composition contains an alkali metal borate and and alkali metal gentisate.

4. The process of claim 1 wherein said mixture is incubated for between about 15 and 21 hours.

5. A reducing composition suitable for being radiolabeled with technetium-99m made by the process according to claim 1.

6. The composition of claim 5 which is lyophilized.

7. The composition of any one of claims 5 or 6 wherein said protein is radiolabeled with technetium-99m.

8. The composition of claim 5 wherein said protein is anti-hCG.

9. The composition of claim 5 wherein said protein is anti-hCG-beta.

10. The composition of any one of claims 5 or 6 wherein said protein, stannous ion and buffer are incubated for a period of time of between about 15 and about 20 hours.

11. The composition of any one of claims 5 or 6 wherein said protein, stannous ion and buffer are incubated for a period of time of between about 15 and about 21 hours and wherein said protein is radiolabeled with technetium-99m.

12. The composition of any one of claims 5 or 6 wherein said buffering composition contains an alkali metal borate and an alkali metal gentisate.

13. The composition of any one of claims 5 or 6 wherein said buffering composition contains an alkali metal borate and an alkali metal gentisate and wherein said protein is radiolabeled with technetium-99m.

14. The composition of any one of claims 8 or 9 wherein said buffering composition contains an alkali metal borate and an alkali metal gentisate.

15. A diagnostic kit suitable for forming a composition to be administered to a human patient which comprises a first sterile package containing a source of stannous ion and a buffering composition comprising a mixture of an alkali metal biphthalate and an alkali metal tartrate having a pH between about 4.5 and 8.5 and a second sterile package containing a protein suitable for being radiolabeled with technetium-99m.

16. The kit of claim 15 wherein the composition contained within the first sterile package is lyophilized.

17. The diagnostic kit of any one of claims 15 or 16 wherein said first sterile package contains an alkali metal borate and an alkali metal gentisate.

* * * * *